United States Patent [19]

Noske et al.

[11] Patent Number: 4,971,039
[45] Date of Patent: Nov. 20, 1990

[54] LITHOTRIPSY WORK STATION

[75] Inventors: Erich Noske, Weiher; Franz Plisek, Erlangen; Manfred Rattner, Buckenhof, all of Fed. Rep. of Germany

[73] Assignee: Siemens Aktiengesellschaft, Berlin and Munich, Fed. Rep. of Germany

[21] Appl. No.: 112,562

[22] Filed: Oct. 22, 1987

[30] Foreign Application Priority Data

Oct. 22, 1986 [DE] Fed. Rep. of Germany ....... 3635974

[51] Int. Cl.$^5$ ............................................. A61B 17/22
[52] U.S. Cl. ................................................. 128/024 A
[58] Field of Search .................... 128/653, 24 A, 328; 378/65, 198; 600/127–128

[56] References Cited

U.S. PATENT DOCUMENTS

| | | | |
|---|---|---|---|
| 3,735,755 | 5/1973 | Eggleton et al. | 128/24 A |
| 3,790,805 | 2/1974 | Foderaro | 378/198 |
| 4,137,777 | 2/1979 | Haverl et al. | |
| 4,479,498 | 10/1984 | Toftness | 128/653 |
| 4,539,989 | 9/1985 | Forssmann et al. | 128/328 |
| 4,543,959 | 10/1985 | Sepponen | 128/653 |
| 4,610,249 | 9/1986 | Makofski et al. | 128/328 |
| 4,705,026 | 11/1987 | Chaussy et al. | 128/24 A |
| 4,747,119 | 5/1988 | Heinz et al. | 378/198 |
| 4,763,652 | 8/1988 | Brisson et al. | 128/24 A |
| 4,796,613 | 1/1989 | Heumann et al. | 128/328 |
| 4,821,729 | 4/1989 | Makufski et al. | 128/24 A |

FOREIGN PATENT DOCUMENTS 0206331 12/1986 European Pat. Off. ............ 128/328
8528785.7 7/1986 Fed. Rep. of Germany .
1087356 2/1955 France .

OTHER PUBLICATIONS

Siemens Sale Brochure "Lithostar", A91001-M10-27-G490-01, 1986.

Primary Examiner—William E. Kamm
Assistant Examiner—John D. Zele
Attorney, Agent, or Firm—Hill, Van Santen, Steadman & Simpson

[57] ABSTRACT

A lithotripsy work station having a patient support table and an adjustable mounting arrangement for the shockwave generator which has a coupling chamber with a membrane for coupling the shockwave generator to the patient characterized by the mounting arrangement positioning the shockwave generator directly above the patient supporting table. The shockwave generator can be mounted by a holder which rotates around a vertical axis above the patient supporting table so that a longitudinal axis of the generator can be aligned to intersect with the vertical axis roughly through the center of the patient supporting table. The mounting means can also be a separate holder which is movable in a horizontal direction that is secured to a ceiling in the room or is on a unit movable on the floor. In each of the embodiments, the shockwave generator can be mounted by an adjustable mechanism that allows changing the angle between the vertical axis and the longitudinal axis of the generator.

13 Claims, 4 Drawing Sheets

LITHOTRIPSY WORK STATION

BACKGROUND OF THE INVENTION

The present invention is directed to a lithotripsy work station which has a patient supporting table and an adjustably mounted shockwave generator which has a coupling chamber with a membrane for contacting a surface of the patient.

A known lithotripsy work station has two adjustable shockwave generators, which are arranged under the patient supporting table. One of the generators is applied to the patient from below through an opening in the patient support table in accordance with which kidney is to be treated. A two-plane x-ray means is provided for locating the calculus or kidney stone to be treated.

SUMMARY OF THE INVENTION

An object of the present invention is to simplify a lithotripsy work station in comparison to previously known work stations, particularly to construct it so that the calculi in various positions in the patient, for example, calculi in the left and right kidneys can be optionally treated with the assistance of a single shockwave generator.

To accomplish these objects, the present invention is directed to an improvement in a lithotripsy work station, which has a patient supporting table and an adjustably mounted shockwave generator which has a coupling chamber with a membrane to contact the patient. The improvements are that the shockwave generator is adjustably mounted above the patient supporting table.

In the lithotripsy work station of the invention, a single shock wave generator suffices for the treatment of different calculi, since it can be brought into respective suitable positions above the patient supporting table. In addition, a recess or opening in the patient supporting table is not required because the shock wave generator is not applied to the patient from below but from above.

In an expedient development of the invention, the shockwave generator is secured to a holder which is rotatable around a vertical axis above the patient supporting table and is constructed so that a longitudinal axis of the shockwave generator intersects the vertical axis proceeding roughly through the center of the patient supporting table. Given this design, the shockwave generator can be swiveled around the vertical axis with the assistance of the holder and can, thus, be brought into the respective desired position.

An advantage of the invention is that a universal adjustment of the shockwave generator is possible. This arrangement comprises that the shockwave generator is mounted on a holder adjustable in the direction of the longitudinal axis of the shockwave generator and also in a vertical direction. The supply or power unit for the shockwave generator can be accommodated in the holder so that an especially compact structure for the overall work station occurs.

A locating system comprising two x-ray units can be present for locating the respective calculus or stone. The central ray of each of the two x-ray units lie in a vertical plane in which the longitudinal axis of the patient support table also lies. The location system and holder for the shockwave generator can comprise a shared suspension above the patient supporting table. However, it is also possible to individually suspend the holder and the locating system above the patient supporting table.

Another possibility or modification of the invention is that the holder is secured to a stand displaceable on the floor. In this case it extends over the patient supporting table.

It is also advantageous to mount the shockwave generator on the holder so that the angle between its axis and the vertical axis is adjustable. An optimum adjustment of the shockwave generator is, thus, possible.

Finally, another modification is to interchangeably secure the shockwave generator in the holder. It is also possible that one or both of the x-ray units can be augmented or replaced by ultrasound locating systems for the purpose of locating the stone or calculus.

Other advantages and features of the invention will be readily apparent from the following description of the drawings, the preferred embodiment and the claims.

DESCRIPTION OF THE PREFERRED EMBODIMENTS

Figure 1:
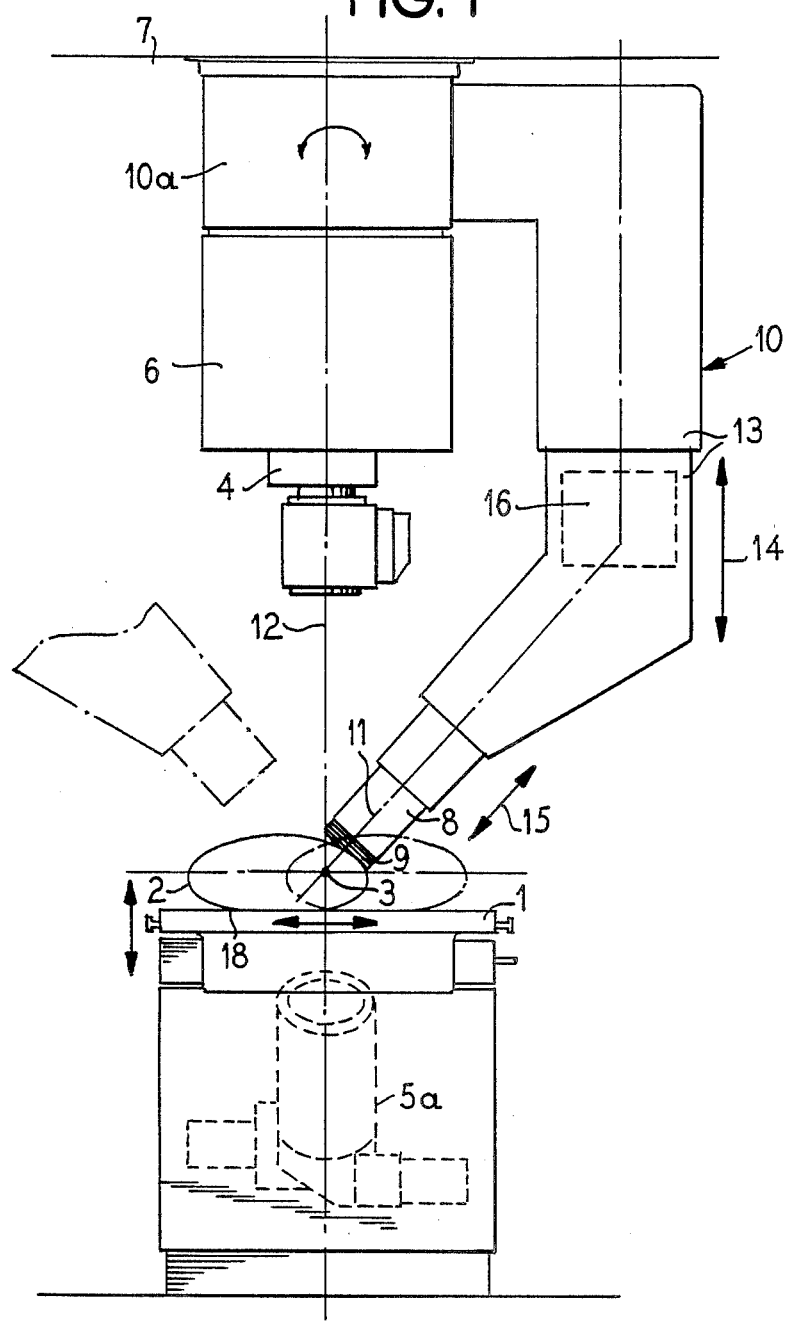
FIG. 1 is an end view of a lithotripsy work station in accordance with the present invention.
Figure 2:
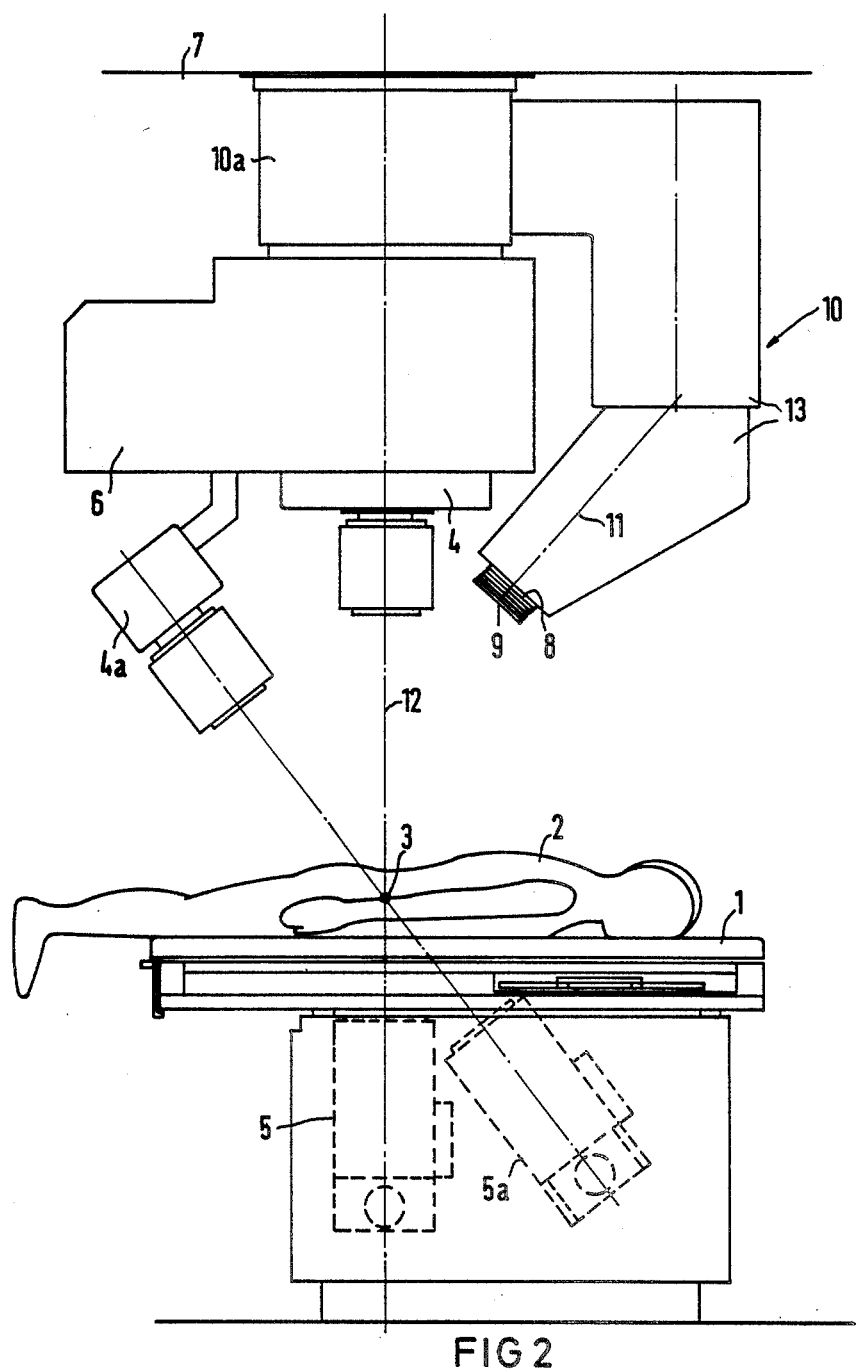
FIG. 2 is a side view of the work station of FIG. 1.

The principles of the present invention are particularly useful when incorporated into a lithotripsy work station, illustrated in FIGS. 1 and 2. The work station has a patient supporting table 1 on which a patient 2 is positioned to lie on the patient's stomach so that a calculus or kidney stone is positioned in an isocenter 3 for disintegration. The work station includes means for locating the kidney stone, which is illustrated in FIGS. 1 and 2 as a two-level x-ray examination installation having a pair of x-ray radiators or x-ray sources 4 and 4a (best illustrated in FIG. 2) and x-ray image intensifiers 5 and 5a with the following video chain. The use of x-ray radiation and x-ray intensifiers of this type are disclosed in copending U.S. patent application Ser. No. 912,043, filed Sept. 26, 1986, which includes the disclosure of German Gebrauchsmuster No. G 85 28 785.7 and which issued as U.S. Pat. No. 4,796,613 on Jan. 10, 1989. The x-ray radiator or source 4 and the image intensifier 5 lie on a vertical axis 12, while the x-ray radiator or source 4a and the image intensifier 5a are on an axis which forms an angle with the vertical axis 12, but coincide at the isocenter 3.

As best illustrated in FIG. 2, the x-ray radiators 4 and 4a are mounted in a housing 6 that is secured to a stand 7, which is suspended in an adjustable manner in a vertical direction. For the purposes of disintegrating calculi in the body of the patient 2, a shockwave generator 8, which has a coupling chamber with a membrane 9 which can be brought into contact with the skin of the patient, is provided. As illustrated in FIGS. 1 and 2, the shock generator 8 is mounted on a holder 10 so that the longitudinal axis 11 of the shockwave generator will intersect the vertical axis 12 at isocenter 3. The vertical axis 12 proceeds roughly through the center of the supporting table 1 and also proceeds through the center, as mentioned hereinbefore, of the x-ray source 4. The holder 10 is pivotable around an angle of 180° on the vertical axis 12, due to being mounted by a bearing 10a whose axis is the axis 12. The shockwave generator is connected to the holder 10 in an adjustable manner and can be displaced in the direction of the longitudinal axis 11, as illustrated by the double arrows 15. In addition, a vertical arm or part 13 of the holder 10 is extensible in a telescopic fashion in the direction of the double arrow 14, which is parallel to the vertical axis 12, so that the shockwave generator 8 is also adjustable in the vertical direction.

For the treating of a calculus in the body of the patient 2, the shockwave generator 8 is, first, brought to the side of the patient in which the calculus lies by pivoting the holder 10 around the axis 12. Subsequently, the calculus to be treated is brought into the focus of the shockwave generator 8 by adjusting the shockwave generator along the directions indicated by the double arrows 14 and 15. The generation of the shockwaves for disintegrating the calculus can now occur.

In the position of the shockwave generator, shown in solid lines, a treatment of the kidney stone lying on the left side of the patient is possible. The patient is thereby situated to lie and prone on the table 1. When a calculus is to be treated in the right kidney, then the holder 10 is swiveled through 180° around the vertical axis 12 (shown in chain lines in FIG. 1). The treatment of the calculi in different positions is, thus, possible with the assistance of a single shockwave generator without repositioning the patient 2. The application of the shockwave is possible in addition to a percutaneous litholapaxy (PCL). The treatment and disintegration of gall stones can also be carried out with this device. While treating gall stones, the patient is brought into a supine position on the table 1. The patient supporting table 1 is a simple table which can be fashioned relatively narrow. As shown, the holder 10 can be mounted on a stand, but can also be held on the ceiling of the treatment room.

When a shockwave treatment is not being provided, then the shockwave generator 8 can be displaced into an upper parking or retracted position by movement along the two directions indicated by the double arrows 14 and 15, which retracted position is illustrated in FIG. 2, and which will provide clearance for access to the patient. The supply unit 16, which includes the controls and the power supply, can be accommodated in a vertical arm or part 13 of the holder 10 in a space saving fashion.

Figure 4:
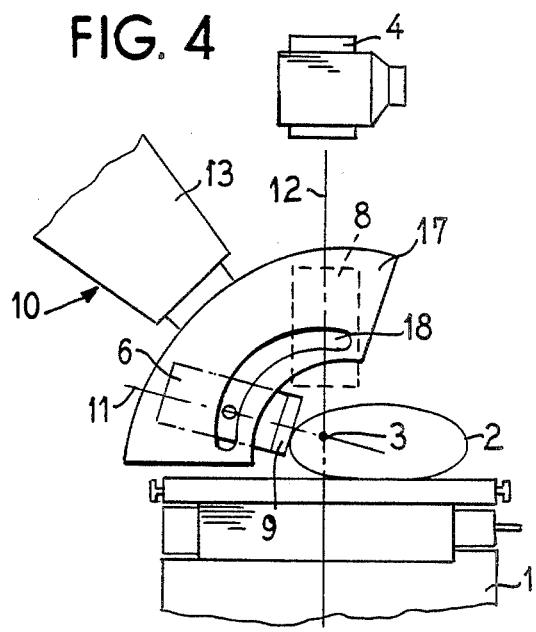
FIG. 4 is a partial end view showing a modification of the work station of FIG. 1.

An expansion of the exemplary embodiment according to FIGS. 1 and 2 comprises, as shown in FIG. 4, wherein the shockwave generator 8 is connected to the holder 10 in an adjustable fashion, so that the angle between the axis 11 and the axis 12 is adjustable. According to FIG. 4, this is obtained by a guide 17, which is connected to the holder at the end thereof. The guide 17 has a guide path or arcuate path 18, which is a sector of a circle having a center on the isocenter 3. By swiveling the shockwave generator 8 on the guide path 18, accordingly, the angle of the shockwave generator 8 to the vertical axis 12 can be adjusted.

In FIG. 4, the lower part of the holder 10 on the left side of the axis 12 is shown with the modification comprising the guide 17 for adjustably mounting the shockwave generator with one position in bold lines and another shown in dotted lines. In FIG. 1 with the shockwave generator 8 on the left side, the generator 8 can treat a calculi on the left side of the patient 2 who will preferably be in a position illustrated in chain lines in FIG. 1.

Figure 3:
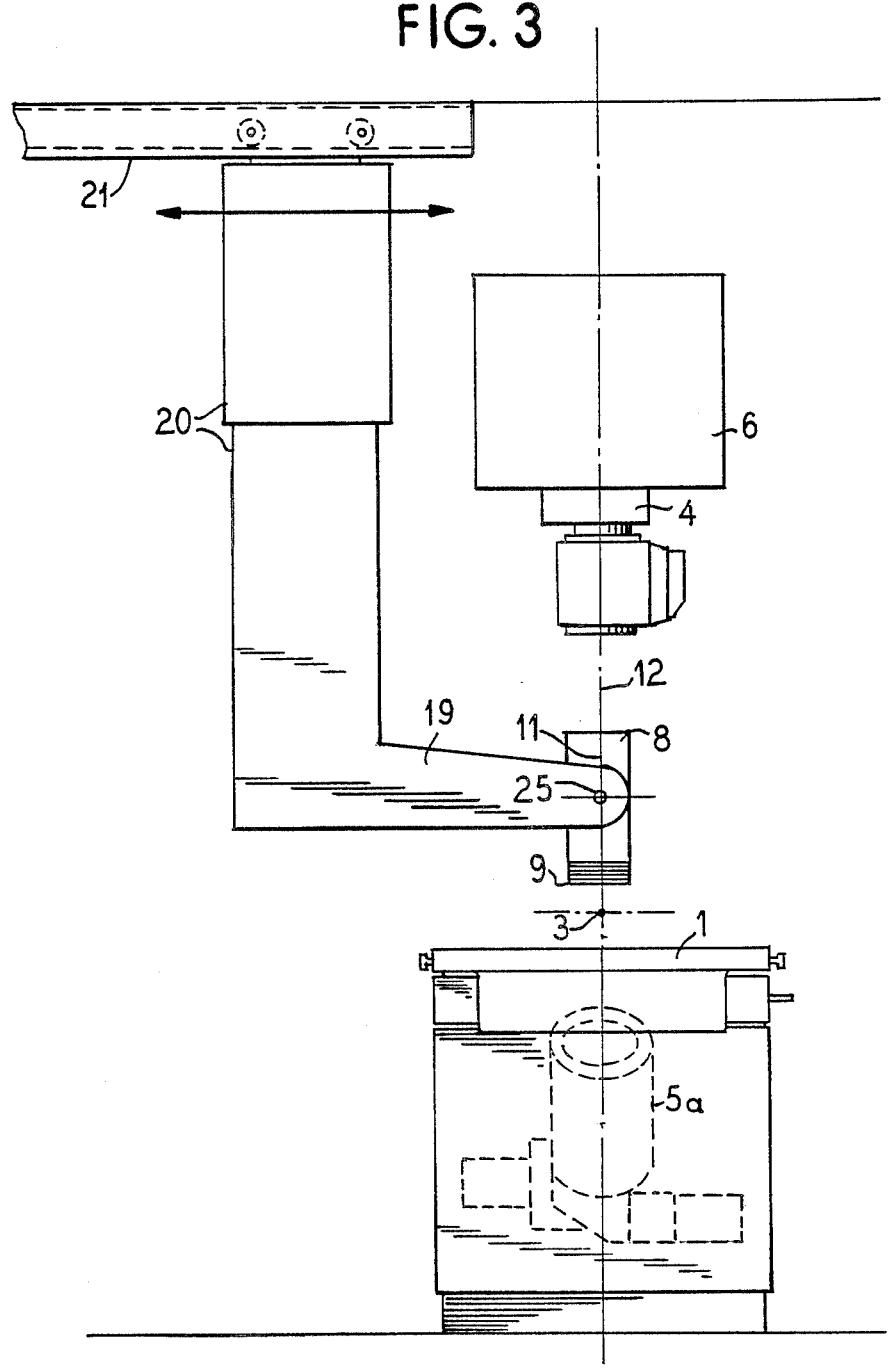
FIG. 3 is an end view of the embodiment of a lithotripsy work station according to the present invention.

In the embodiment illustrated in FIG. 3, the shockwave generator 8 is secured on an arm 19 to swivel or pivot around a horizontal axis 25. This arm 19 is secured to a stand 20, which is extensible in a telescopic fashion and is displaceable in a ceiling track 21. The adjustment of the shockwave generator 8, thereby, occurs by displacing the stand 20 and by swiveling the shockwave generator around a horizontal axis 25 in such a fashion that the longitudinal axis 11 of the shockwave generator 8 always proceeds through the isocenter 3. An alternative mounting possibility for the angle between the longitudinal axis 11 and the shockwave generator 8 and the axis 12, which extends vertically through the x-ray unit 4, is to provide the arm 19 (FIG. 5) with a guide 22, which has an arcuate guide path 23. As in the previously discussed guide 17 with arcuate path 18, the center of the path 23 lies on the isocenter 3. As a result, the shockwave generator 8 is adjustable in view of the angle between the axes 11 and 12 without adjustment of the stand 20 on the track 21, which occurs when the generator is mounted for pivoting movement on the axis 25.

Figure 5:
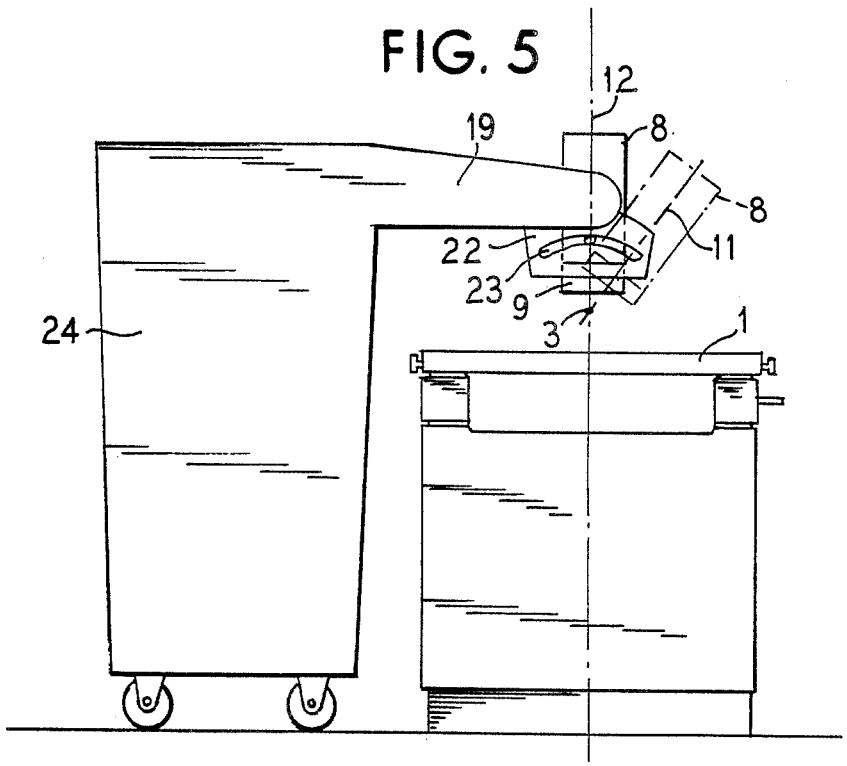
FIG. 5 is a partial end view showing a modification of the work station of FIG. 3.

FIG. 5 also shows the modification wherein the arm 19 is mounted on a stand 24, which is displaceable on the floor.

All exemplary embodiments have a common feature that a locating system comprising two x-ray sources 4 and 4a and their intensifiers 5 and 5a are present and that central rays of the beams of x-rays emitted from the sources 4 and 4a lie in a vertical plane in which the longitudinal axis of a patient supporting table 1 also lies. In the examples of FIGS. 1 and 2, the locating system comprising the x-ray sources 4 and 4a with the intensifiers 5 and 5a and the holder 10 for the shockwave generator comprise a common suspension or mounting system over the table 1. In the embodiment of FIG. 3, the locating system of the x-ray sources 4 and 4a, with their intensifiers 5 and 5a, and the shockwave generator 8 are individually mounted above the patient supporting table 1.

It is possible to releasably mount the shockwave generator in an interchangeable fashion. For example, this can occur in the embodiment of FIG. 3, wherein means for releasably mounting the generator are provided at the axis 25 to allow removal of the generator.

It is also possible for the locating means to include one or more ultrasonic locating systems. These can be in addition to the x-ray locating units 4 and 4a or replace the x-ray units 4 and 4a.

Although various minor modifications may be suggested by those versed in the art, it should be understood that we wish to embody within the scope of the patent granted hereon all such modifications as reasonably and properly come within the scope of our contribution to the art.

We claim:

1. In a lithotripsy work station comprising a patient supporting table and an adjustably mounted shockwave generator having means including a membrane adapted for contacting a patient, the improvements comprising means for adjustably mounting the shockwave generator above said patient supporting table, said means for adjustably mounting the shockwave generator including a holder rotatable around a vertical axis above said patient supporting table, said holder mounting the shockwave generator with a longitudinal axis of the generator forming an angle with the vertical axis and intersecting the vertical axis roughly at a point adjacent the patient supporting table.

2. In a lithotripsy work station according to claim 1, wherein said holder includes means for adjustably positioning the shockwave generator along the longitudinal axis.

3. In a lithotripsy work station according to claim 2, wherein the holder includes means for adjusting the shockwave generator along said vertical axis.

4. In a lithotripsy work station according to claim 1, wherein the holder includes means for adjusting the shockwave generator along said vertical axis.

5. In a lithotripsy work station according to claim 1, wherein a power supply unit for the shockwave generator is mounted in said holder.

6. In a lithotripsy work station according to claim 3, wherein said point is at the center of the patient supporting table.

7. In a lithotripsy work station having a patient supporting table, a single shockwave generator having a longitudinal axis and a coupling chamber with a membrane adapted for contacting a patient, and means for mounting the shockwave generator, the improvements comprising the means for mounting the shockwave generator positioning the shockwave generator above the patient supporting table for movement around a vertical axis with the longitudinal axis forming an angle with the vertical axis and said means for mounting including first means for adjusting a vertical position of the shockwave generator above the table along said vertical axis and second means for adjusting a position of the shockwave generator in a direction along said longitudinal axis.

8. In a lithotripsy work station according to claim 7, wherein the means of mounting includes a holder mounted for pivotal movement around said vertical axis, said holder having an arm with a first telescopic portion and a second telescopic portion, said first telescopic portion forming the first means and the second telescopic portion extending at said angle and forming said second means.

9. In a lithotripsy work station according to claim 8, which includes a locating system having two x-ray units, said x-ray units being mounted with a central ray of a beam of x-ray radiation emitted from each unit lying in a vertical plane in which a longitudinal axis of the patient supporting table also lies, said locating system and said holder comprising a common suspension above said patient supporting table.

10. In a lithotripsy work station comprising a patient supporting table and a single shockwave generator having a longitudinal axis and means adapted for contacting a patient including a membrane, the improvements comprising means for adjustable mounting the shockwave generator for movement around a vertical axis above said patient supporting table with said longitudinal axis forming an angle with the vertical axis.

11. A lithotripsy work station comprising a patient supporting table having a surface adapted to receive a patient, a shockwave generator, and means for adjustably positioning said shockwave generator to move around a vertical axis above said surface of the patient supporting table.

12. A lithotripsy work station according to claim 11, wherein said means for positioning the shockwave generator includes a holder rotatable around the vertical axis above said patient supporting table, said holder mounting the shockwave generator with a longitudinal axis of the generator intersecting the vertical axis at a point above the surface of the patient supporting table.

13. A lithotripsy work station according to claim 12, which includes a locating system having two x-ray units, said x-ray units being mounted with a central ray of a beam of x-ray radiation emitted from each unit lying in a vertical plane in which a longitudinal axis of the patient supporting table also lies, said locating system and said holder comprising a common suspension above said patient support table.

* * * * *